US009958380B2

(12) United States Patent
Saptari

(10) Patent No.: US 9,958,380 B2
(45) Date of Patent: May 1, 2018

(54) SYSTEMS, METHODS, AND APPARATUS FOR OPTICAL HYDROCARBON GAS COMPOSITION MONITORING

(71) Applicants: MKS Instruments, Inc., Andover, MA (US); Pason Systems Corp., Calgary (CA)

(72) Inventor: Vidi Saptari, Cambridge, MA (US)

(73) Assignees: MKS Instruments, Inc., Andover, MA (US); Pason Systems Corp., Calgary, CA (US)

( * ) Notice: Subject to any disclaimer, the term of this patent is extended or adjusted under 35 U.S.C. 154(b) by 3 days.

(21) Appl. No.: 14/753,366

(22) Filed: Jun. 29, 2015

(65) Prior Publication Data

US 2015/0377774 A1    Dec. 31, 2015

Related U.S. Application Data

(60) Provisional application No. 62/019,401, filed on Jun. 30, 2014.

(51) Int. Cl.
*G01N 21/35* (2014.01)
*G01N 21/3504* (2014.01)
(Continued)

(52) U.S. Cl.
CPC ....... *G01N 21/3504* (2013.01); *G01N 21/359* (2013.01); *G01N 2021/3155* (2013.01); *G01N 2021/3595* (2013.01)

(58) Field of Classification Search
CPC .................................................. G01N 21/3504
See application file for complete search history.

(56) References Cited

U.S. PATENT DOCUMENTS 5,717,209 A * 2/1998 Bigman ............... G01N 21/359
250/339.12
5,822,058 A   10/1998 Adler-Golden et al.
(Continued)

FOREIGN PATENT DOCUMENTS

WO    WO-2015/054594 A1    4/2015

OTHER PUBLICATIONS

Van Agthoven, M. A. et al., Near-Infrared Spectral Analysis of Gas Mixtures, Applied Spectroscopy, 56(5):593-598 (2002).
(Continued)

*Primary Examiner* — Edwin Gunberg
(74) *Attorney, Agent, or Firm* — Choate, Hall & Stewart LLP; William R. Haulbrook; Margo R. Monroe

(57) ABSTRACT

The disclosure relates to spectroscopic systems and spectrometers configured for hydrocarbon gas composition monitoring which provides compound speciation capability and function. In certain embodiments, the system identifies two or more bands of spectral data—e.g., including a band in each of (i) the near infrared and (ii) mid infrared wavelength regions, though bands covering subsets from about 800 nm to about 12 μm can be used—from the signal corresponding to the hydrocarbon fluid in the gas flow cell, where the two or more bands are not contiguous (e.g., there is at least a 50 nm separation between the nearest ends of two bands). A combined spectrum is then formed from the two or more non-contiguous bands of spectral data and processed to identify and/or quantify the constituents of the hydrocarbon fluid.

30 Claims, 8 Drawing Sheets

(51) Int. Cl.
*G01N 21/359* (2014.01)
*G01N 21/31* (2006.01)

(56) References Cited

U.S. PATENT DOCUMENTS

| | | |
|---|---|---|
| 6,555,820 B1 | 4/2003 | Tacke et al. |
| 8,184,293 B2 | 5/2012 | Bonyuet et al. |
| 8,502,981 B2 | 8/2013 | Bonyuet et al. |
| 8,884,215 B2 * | 11/2014 | Gunn ................ G01N 33/2823 250/253 |
| 8,896,839 B2 | 11/2014 | Saptari |
| 2006/0038997 A1 * | 2/2006 | Julian ...................... G01J 3/02 356/328 |
| 2008/0078544 A1 * | 4/2008 | Christian ................. G01J 3/02 166/264 |
| 2010/0290045 A1 | 11/2010 | Saptari |
| 2011/0211193 A1 | 9/2011 | Saveliev et al. |
| 2013/0334412 A1 | 12/2013 | Gunn et al. |

OTHER PUBLICATIONS

International Search Report, PCT/US2015/038268, 4 pages, dated Sep. 8, 2015.
Written Opinion, PCT/US2015/038268, 9 pages, dated Sep. 8, 2015.

* cited by examiner

US 9,958,380 B2

SYSTEMS, METHODS, AND APPARATUS FOR OPTICAL HYDROCARBON GAS COMPOSITION MONITORING

CROSS-REFERENCE TO RELATED APPLICATIONS

This application claims priority to and the benefit of, and incorporates herein by reference in its entirety, U.S. Provisional Patent Application No. 62/019,401, filed Jun. 30, 2014, titled "Optical Hydrocarbon Gas Composition Monitoring."

FIELD OF THE INVENTION

The invention relates generally to spectroscopic systems and spectrometers for hydrocarbon gas monitoring. More particularly, in certain embodiments, the invention relates to spectroscopy systems for speciation of alkane gases for composition monitoring of natural gas and other similar gas mixtures, including other types of fuel gases. More particularly, in certain embodiments, the invention relates to methods and systems for measuring and/or monitoring the heating value, energy content, and/or calorific value, as well as other physical and chemical properties derived from the chemical composition, of a sample gas.

BACKGROUND

The composition of natural gas and other hydrocarbon fuel gases is often identified to determine its energy content, heating value, specific gravity, Wobbe index, and/or other properties. The composition measurement may be performed during exploration and mining, manufacturing processes in refineries, as part of quality assurance/control during buy/sell transactions, as well as during its use in power or electricity generation. Composition is typically determined using gas chromatography (GC), where physical separation of the constituents of the sample gas is performed by flowing the gas sample through a thin long column. After the constituents of the sample gas move through the GC column, they reach a detector that provides a measured response proportional to the concentration of each compound. Drawbacks of current GC techniques include: (i) long separation time and thus long measurement time, (ii) requirement of a carrier gas which may be expensive to obtain and maintain, and (iii) poor measurement stability, requiring frequent recalibration.

Moreover, hydrocarbon gases absorb electromagnetic light radiation in several wavelength bands in the near infrared and in the mid infrared. The absorption signals may be used to perform correlation analysis with the energy content or heating value of the sample hydrocarbon gas, as described, for example, in U.S. Pat. No. 6,555,820 to Tacke et. al and U.S. Pat. No. 5,822,058 to Adler-Golden et. al. Many products in the market, to-date, use infrared absorption signals of hydrocarbon gases to determine presence of combustible gases and vapors in the ambient or surrounding air. However, spectral speciation of the constituents of a hydrocarbon gas mixture is a challenging task given the overlapping nature of the hydrocarbon spectra. FIG. 2 shows example absorption spectra of C1-C4 alkane gases in the near infrared (NIR), specifically between 1600 nm and 1900 nm. As shown, although the individual constituents have unique shapes or spectral features, they significantly overlap one another. Furthermore, the spectra of C2, C3 and C4's (ethane, propane and butanes) are broad and have limited distinguishing features from each other.

Thus, there is a need for an improved method and system for monitoring the composition of hydrocarbon gases.

SUMMARY OF THE INVENTION

The present disclosure provides a spectroscopic system for the composition measurement of hydrocarbon gas, such as natural gas, biogas, and other fuel gases containing alkanes. The spectroscopic system employs absorption measurements from about 800 nm to about 12 µm (e.g., from about 800 nm to about 12 µm for non-dispersive infrared systems (NDIR), or from about 1.5 µm to about 12 µm for Fourier Transform infrared systems (FTIR). Mixture constituents such as methane, ethane, propane, n-butane, iso-butane, etc., are speciated via a spectral decomposition technique, and, in certain embodiments, the concentration of each constituent is reported on an independent measurement channel or readout.

Two or more non-contiguous bands of spectral data are identified from a spectral signal. A combined spectrum is then formed from the two or more non-contiguous bands of spectral data and processed to identify and/or quantify the constituents of the hydrocarbon gas mixture. This technique is found to provide surprisingly increased accuracy, and the ability to differentiate between two species with similar spectra, for example, n-butane and n-pentane, in mixtures containing both species.

An optics-based sensor/analyzer determines the composition of fuel gases to enable the real-time monitoring of the gases, at the process line or pipeline, and without the need for operator intervention (via remote deployment). Additionally, in certain embodiments, the system does not require a carrier gas, or other consumables, nor expensive infrastructure for its operation.

In one aspect, the invention is directed to a spectrometer system for speciation and/or quantitative determination of constituents of a hydrocarbon fluid, the spectrometer system comprising: a broadband light source; a gas flow cell through which the hydrocarbon fluid flows and through which (or to which) light from the light source passes; an optical detector for receiving the light after transmission through (or reflection from) the hydrocarbon fluid flowing through the gas flow cell and for generating a scan signal indicative of spectral information of the detected light over a continuous broadband region or over multiple discrete wavelength bands, where the scan covers a range that is equivalent to, is a subset of, or overlaps, the range from about 800 nm to about 12 µm; a processor; and a non-transitory computer readable medium storing instructions thereon, wherein the instructions, when executed, cause the processor to: identify two or more bands of spectral data from the signal corresponding to the hydrocarbon fluid in the gas flow cell, wherein the two or more bands are non-contiguous; and process data from the two or more bands of spectral data to speciate and/or quantify one or more constituents (e.g., one, two, three, four, or five constituents) of the hydrocarbon fluid.

In certain embodiments, the hydrocarbon fluid is a natural gas, a natural gas liquid, or a biogas. In certain embodiments, the hydrocarbon fluid comprises one or more of species C1-C6, in any combination.

In certain embodiments, the broadband light source comprises a blackbody source and/or one or more LEDs.

In certain embodiments, the system further comprises a spectral unit for dividing a light beam received from the broadband light source into multiple discrete wavelength bands, wherein the spectral unit and gas flow cell are situated such that the light beam passes from the broadband light source through the spectral unit, then the divided beam passes through the gas flow cell. In certain embodiments, the system further comprises a spectral unit for dividing a light beam received from the broadband light source into multiple discrete wavelength bands, wherein the spectral unit and gas flow cell are situated such that light passes from the broadband light source through the gas flow cell, then through the spectral unit. In certain embodiments, the spectral unit comprises at least one member selected from the group consisting of an interference filter array, a linear variable filter (LVF), a grating, a scanning interferometer, and a Fabry-Perot etalon.

In certain embodiments, the optical detector comprises a wide-scanning spectrometer. In certain embodiments, the optical detector comprises a Fourier transform infrared (FTIR) spectrometer. In certain embodiments, the optical detector comprises a non-dispersive infrared (NDIR) detector.

In certain embodiments, there is at least a 50 nm separation between the nearest ends of two bands of the two or more bands.

In certain embodiments, the instructions cause the processor to identify a first band of spectral data that is a subset of 1300 nm to 1800 nm and a second band of spectral data that is a subset of 1850 nm to 2500 nm. In certain embodiments, the instructions cause the processor to identify a first band of spectral data spanning from about 1500 nm to about 1780 nm and a second band of spectral data spanning from about 1900 nm to about 2200 nm (e.g., where "about" means+/−50 nm).

In certain embodiments, the instructions cause the processor to speciate and quantify one or more constituents of the hydrocarbon fluid (e.g., hydrocarbon gas), including n-pentane. In certain embodiments, the hydrocarbon fluid comprises n-pentane and n-butane, and the instructions cause the processor to speciate and quantify at least n-pentane and n-butane. In certain embodiments, the hydrocarbon fluid contains no greater than 1.0% n-pentane. In certain embodiments, the hydrocarbon fluid contains at least 5% n-butane.

In certain embodiments, the instructions cause the processor to identify a first band of spectral data that is a subset of 1600 nm to 1900 nm and a second band of spectral data that is a subset of 2100 nm to 2600 nm. In certain embodiments, the hydrocarbon fluid comprises at least one C6-or-higher species (e.g., a hexane or a heptane) and the instructions cause the processor to speciate and quantify the C6-or-higher species.

In certain embodiments, the two or more bands comprise a band from about 3100 nm to about 3600 nm (e.g., where "about" means+/−100 nm), and the instructions cause the processor to speciate and quantify a component of the hydrocarbon fluid that is present in a concentration no greater than 0.1%.

In certain embodiments, the instructions cause the processor to identify a bulk composition-range measurement of at least one component (e.g., from 0.1 to 100 wt. %) and a trace-range measurement of at least another component (e.g., from 0 to 0.1 wt. %).

In certain embodiments, the two or more non-contiguous bands comprise at least one near-infrared band (e.g., a band that is, or is a subset of, the range from about 1600 nm to about 1900 nm, and/or a band that is, or is a subset of, the range from about 2200 nm to about 2500 nm) and a mid-infrared band (e.g., a band that is, or is a subset of, the range from about 3100 nm to about 3600 nm), and wherein the instructions cause the processor to identify a bulk composition-range measurement of at least one component (e.g., from 0.1 to 100 wt. %) and a trace-range measurement of at least another component (e.g., from 0 to 0.1 wt. %).

In certain embodiments, the instructions cause the processor to identify a primary band of spectral data that is equivalent to, is a subset of, or overlaps, the range from about 1400 nm to about 1900 nm and a secondary band that is equivalent to, is a subset of, or overlaps, the range from about 1900 nm to about 2500 nm, wherein the secondary range is used to identify and/or quantify pentane (e.g., n-pentane) in the hydrocarbon fluid, and wherein the primary range is used to identify and/or quantify one or more of C1, C2, C3, and C4 in the hydrocarbon fluid.

In certain embodiments, the instructions cause the processor to: form a combined spectrum from the two or more non-contiguous bands of spectral data; and process the combined spectrum to identify and/or quantify one or more constituents of the hydrocarbon fluid.

In another aspect, the invention is directed to a method for speciation and quantitative determination of constituents of a hydrocarbon fluid, the method comprising: identifying, by a processor of a computing device, two or more bands of spectral data from a signal corresponding to the hydrocarbon fluid in a gas flow cell, wherein the two or more bands are non-contiguous; and speciating and quantifying, by the processor, one or more constituents (e.g., one, two, three, four, or five constituents) of the hydrocarbon fluid using data from the two or more bands of spectral data.

In certain embodiments, the method further comprises: generating light from a light source (e.g., broadband light source); directing light from the light source through (or to) a gas flow cell; receiving light at an optical detector after transmission through (or reflection from) the hydrocarbon fluid flowing through the gas flow cell; and generating the signal corresponding to the hydrocarbon fluid in the gas flow cell.

In certain embodiments, the hydrocarbon fluid is a natural gas, a natural gas liquid, or a biogas. In certain embodiments, the hydrocarbon fluid comprises one or more of species C1-C6, in any combination.

In certain embodiments, there is at least a 50 nm separation between the nearest ends of two bands of the two or more bands.

In certain embodiments, the identifying step comprises identifying a first band of spectral data that is a subset of 1300 nm to 1800 nm and a second band of spectral data that is a subset of 1850 nm to 2500 nm. In certain embodiments, the identifying step comprises identifying a first band of spectral data spanning from about 1500 nm to about 1780 nm and a second band of spectral data spanning from about 1900 nm to about 2200 nm (e.g., where "about" means+/−50 nm).

In certain embodiments, the method comprises speciating and quantifying one or more constituents of the hydrocarbon fluid (e.g., hydrocarbon gas), including n-pentane. In certain embodiments, the hydrocarbon fluid comprises n-pentane and n-butane, and the method comprises speciating and quantifying at least n-pentane and n-butane. In certain embodiments, the hydrocarbon fluid contains no greater than 1.0% n-pentane. In certain embodiments, the hydrocarbon fluid contains at least 5% n-butane.

In certain embodiments, the identifying step comprises identifying a first band of spectral data that is a subset of 1600 nm to 1900 nm and a second band of spectral data that is a subset of 2100 nm to 2600 nm. In certain embodiments, the hydrocarbon fluid comprises at least one C6-or-higher species (e.g., a hexane or a heptane) and the instructions cause the processor to speciate and quantify the C6-or-higher species.

In certain embodiments, the two or more bands comprise a band from about 3100 nm to about 3600 nm (e.g., where "about" means +/−100 nm), and the instructions cause the processor to speciate and quantify a component of the hydrocarbon fluid that is present in a concentration no greater than 0.1%.

In certain embodiments, the method comprises determining a bulk composition-range measurement of at least one component (e.g., from 0.1 to 100 wt. %) and a trace-range measurement of at least another component (e.g., from 0 to 0.1 wt. %).

In certain embodiments, the two or more non-contiguous bands comprise at least one near-infrared band (e.g., a band that is, or is a subset of, the range from about 1600 nm to about 1900 nm, and/or a band that is, or is a subset of, the range from about 2200 nm to about 2500 nm) and a mid-infrared band (e.g., a band that is, or is a subset of, the range from about 3100 nm to about 3600 nm), and wherein the method comprises determining a bulk composition-range measurement of at least one component (e.g., from 0.1 to 100 wt. %) and a trace-range measurement of at least another component (e.g., from 0 to 0.1 wt. %).

In certain embodiments, the method comprises identifying a primary band of spectral data that is equivalent to, is a subset of, or overlaps, the range from about 1400 nm to about 1900 nm and a secondary band that is equivalent to, is a subset of, or overlaps, the range from about 1900 nm to about 2500 nm, wherein the secondary range is used, by the processor, to identify and quantify pentane (e.g., n-pentane) in the hydrocarbon fluid, and wherein the primary range is used, by the processor, to identify and/or quantify one or more of C1, C2, C3, and C4 in the hydrocarbon fluid.

In certain embodiments, the speciating and quantifying step comprises: forming, by the processor, a combined spectrum from the two or more non-contiguous bands of spectral data; and processing, by the processor, the combined spectrum to identify and/or quantify one or more constituents of the hydrocarbon fluid.

In another aspect, the invention is directed to a spectroscopic system for speciation and/or quantitative determination of constituents of a hydrocarbon fluid (e.g., the fluid containing one or more of species C1-C6, in any combination). The system includes an electromagnetic radiation source (e.g., a light emitter), a spectral unit for dividing the beam into multiple wavelength bands of components, and a light detection unit to convert the light energy into electrical signal (as used herein, the term "light" is not restricted to visible light). The electrical signal containing spectral information is converted into a digital signal, which is received by a digital signal processor or a computer running a spectral decomposition and analysis algorithm. The processor determines the concentration (or other quantification of the amount) of the individual constituents present in the sample gas—such as methane, ethane, propane, etc.—which are reported in a local display unit or communicated to an external monitoring or reporting device, for example, through any of various communication devices and protocols such as USB, TCP/IP, Modbus, RS-485, serial communication, wireless, and the like.

In some embodiments, the spectroscopic system includes a gas cell, e.g., a gas flow cell, to contain the sample gas, sealed with transparent windows, positioned in a direct path of the light beam. The path length of the beam inside the gas flow cell is used to determine the magnitude of the absorption signal for a given constituent concentration, pressure, and temperature, and, in some embodiments, the path length of the gas cell is designed to produce an advantageous signal-to-noise ratio for a given application. In certain embodiments, the gas cell is equipped with a pressure transducer and/or a temperature transducer to continuously measure pressure and/or temperature, respectively, of the sample gas in real time. The measured pressure and temperature values are then used to correct for the sample pressure and temperature variations.

In certain embodiments, the system identifies two or more bands of spectral data—e.g., including a band in each of (i) the near infrared and (ii) mid infrared wavelength regions, though bands covering subsets from about 800 nm to about 12 μm can be used—from the signal corresponding to the hydrocarbon fluid in the gas flow cell, where the two or more bands are not contiguous (e.g., there is at least a 50 nm separation between the nearest ends of two bands).

In certain embodiments, the spectroscopic system operates in the near infrared region, analyzing hydrocarbon bands between 1600 nm and 1900 nm. The spectral unit provides a spectral resolution between 1 nm and 10 nm (e.g., 3 nm-7 nm, e.g., 4 nm-6 nm, e.g., 5 nm), which is found to provide a suitable tradeoff between the signal-to-noise ratio and spectral linearity of the measurement. In certain embodiments, the spectral resolution is adjustable. In some embodiments, with this single region, the spectroscopic system is capable of robustly and accurately speciating C1-C5 of alkane, alkene, and alkyne constituents, including speciation of the isomers.

In some embodiments, for speciation of C6 components and heavier (e.g., hexanes and heptanes), the spectroscopic system operates in the near infrared region, analyzing the hydrocarbon bands, for example, in the 1600-1900 nm region and the 2100-2600 nm region. The addition of the second wavelength region provides additional spectral features to accurately and robustly speciate the C6 components and heavier. The spectral unit provides spectral resolution, in some embodiments, between 1 nm and 10 nm (e.g., 3 nm-7 nm, e.g., 4 nm-6 nm, e.g., 5 nm). In certain embodiments, the spectral resolution is adjustable.

In certain embodiments, the spectroscopic system operates in the mid infrared band (MIR) including, for example, the region between 3100 nm and 3600 nm. Since the hydrocarbon absorption magnitude in this wavelength region is orders of magnitude larger than that in the near infrared (NIR), the spectroscopic system operating in the MIR is well suited for trace level monitoring and composition analysis of hydrocarbon concentrations, e.g., in the parts-per-billion (ppb), parts-per-million (ppm), and/or low percentage (e.g., up to 0.1 wt. %) concentration levels.

In some embodiments, the spectral unit includes a narrow band interference filter array, which includes a number of individual filter elements having bandwidths spanning the operating wavelength range(s) in which each filter transmits only a narrow spectral portion of the light beam. For example, the spectral unit may include 60 filter elements, spanning 300 nm between 1600 nm and 1900 nm, in which each filter has a 5-nm bandwidth or resolution. The bandwidth may be defined as full-width-at-half-height (FWHH) of the narrow band transmission spectra, for example, as illustrated in FIG. 2. Alternatively, the filter may be constructed from a band-pass filter element (referred to as a Linear Variable Filter (LVF)) that has been wedged in one direction to cause the transmission wavelength to vary in linearly in the direction of the wedge.

The filter based spectral unit may include two or more non-contiguous spectral regions. For example, it was found that acquisition of an additional hydrocarbon band, such as the combination band region between 2100 nm and 2600 nm (or a portion thereof), allows for the acquisition of richer spectral features. In some embodiments, the filter element includes two separate wavelength regions, for example, as illustrated in FIG. 3B.

In certain embodiments, the spectral unit includes a diffraction element, such as a grating, to disperse the light beam into multiple adjacent partial spectral bands. The grating is tuned to provide maximum transmission in the hydrocarbon wavelength region(s) of interest. In certain embodiments, the spectral unit includes a scanning interferometer to separate the light beam into its wavelength constituents using Fourier transform spectroscopy.

In another aspect, the present disclosure describes a spectrometer system for speciation and/or quantitative determination of constituents of a hydrocarbon fluid (e.g., the fluid containing one or more of species C1-C6, in any combination). The spectrometer system includes a broadband light source (e.g., a blackbody source, or one or more LEDs). In certain embodiments, the system includes a spectral unit (e.g., an interference filter array, a linear variable filter (LVF), a grating, or a scanning interferometer, e.g., a Fabry-Perot etalon) for dividing a light beam received from the broadband light source (either directly or indirectly, e.g., the light beam entering the spectral unit directly from the source, or after it has passed through the sample) into multiple discrete bands.

The system includes a gas flow cell through which the hydrocarbon fluid flows and through which light from the light source (directly or indirectly) and, optionally, from the spectral unit, passes. The system includes an optical detector for receiving the light (directly or indirectly) after transmission through the hydrocarbon fluid flowing through the gas flow cell and for generating a scan signal indicative of spectral information of the detected light over a continuous broadband region (e.g., via a wide-scanning spectrometer, e.g., Fourier transform spectrometer) or over the multiple discrete bands (e.g. obtaining a spectral scan encompassing a near infrared region), where the scan covers a range that is equivalent to, is a subset of, or overlaps, the range from about 800 nm to about 12 µm (e.g., from about 800 nm to about 12 µm for NDIR, or from about 1.5 µm to about 12 µm for FTIR).

In certain embodiments, the system includes a processor and a non-transitory computer readable medium storing instructions thereon. The instructions, when executed, cause the processor to identify two or more bands of spectral data from the signal corresponding to the hydrocarbon fluid in the gas flow cell, where the two or more bands are not contiguous (e.g., identify a first band of spectral data from about 1600 nm to about 1900 nm and a second band from about 2200 nm to about 2500 nm) (e.g., and where the two or more bands exclude the range 1950 nm to 2150 nm). The instructions, when executed, cause the processor to form a combined spectrum from the two or more non-contiguous bands of spectral data (e.g., by stitching together the two or more bands). The instructions, when executed, cause the processor to process the combined spectrum (e.g., via partial least-squares, classical least-square, or principal component regression analysis) to identify and/or quantify the constituents of the hydrocarbon fluid.

In certain embodiments, the first band overlaps at least 100 nm, or at least 150 nm, or at least 200 nm, or at least 250 nm, of the range from 1600 nm to 1900 nm, e.g., without extending beyond the range of 1600 nm-1900 nm by more than 50 nm, more than 100 nm, more than 150 nm, more than 200 nm, or more than 250 nm. In certain embodiments, the second band overlaps at least 100 nm, or at least 150 nm, or at least 200 nm, or at least 250 nm, of the range from 2200 nm to 2500 nm, e.g., without extending beyond the range of 2200 nm-2500 nm by more than 50 nm, more than 100 nm, more than 150 nm, more than 200 nm, or more than 250 nm. In certain embodiments, the two or more bands exclude the range 1950 nm to 2150 nm.

In certain embodiments, the hydrocarbon fluid is a natural gas, a natural gas liquid, or a biogas.

In certain embodiments, the two or more non-contiguous bands include at least one near-infrared band (e.g., a band from about 1600 nm to about 1900 nm, and/or a band 2200 nm to about 2500 nm) and a mid-infrared band (e.g., a band that is, or is a subset of, the range from about 3100 nm to about 3600 nm), and the instructions cause the processor to identify a composition-range measurement of at least one component (e.g., from 0.1 to 100 wt. %) and a trace-range measurement of at least another component (e.g., from 0 to 0.1 wt. %).

In certain embodiments, the mid-infrared band overlaps at least 100 nm, or at least 150 nm, or at least 200 nm, or at least 250 nm, or at least 300 nm, or at least 350 nm, or at least 400 nm, or at least 450 nm, of the range from 3100 nm to 3600 nm, e.g., without extending beyond the range of 3100 nm-3600 nm by more than 50 nm, more than 100 nm, more than 200 nm, more than 300 nm, or more than 400 nm.

In certain embodiments, the instructions causes the processor to identify a primary band of spectral data that is equivalent to, is a subset of, or overlaps, the range from about 1600 nm to about 1900 nm and a secondary band that is equivalent to, is a subset of, or overlaps, the range from about 2200 nm to about 2500 nm, where the secondary range is used to identify and/or quantify pentane (e.g., n-pentane) in the hydrocarbon fluid, and where the primary range is used to identify and/or quantify one or more of C1, C2, C3, and C4 in the hydrocarbon fluid. In certain embodiments, the mid-infrared band overlaps at least 100 nm, or at least 150 nm, or at least 200 nm, or at least 250 nm, or at least 300 nm, or at least 350 nm, or at least 400 nm, or at least 450 nm, of the range from 3100 nm to 3600 nm, e.g., without extending beyond the range of 3100 nm-3600 nm by more than 50 nm, more than 100 nm, more than 200 nm, more than 300 nm, or more than 400 nm. In certain embodiments, the secondary band overlaps at least 100 nm, or at least 150 nm, or at least 200 nm, or at least 250 nm, of the range from 2200 nm to 2500 nm, e.g., without extending beyond the range of 2200 nm-2500 nm by more than 50 nm, more than 100 nm, more than 150 nm, more than 200 nm, or more than 250 nm.

In another aspect, the present disclosure describes a spectrometer system for speciation and/or quantitative determination of constituents of a hydrocarbon fluid (e.g., the fluid containing one or more of species C1-C6, in any combination). The spectrometer system includes a broadband light source (e.g., a blackbody source, or one or more LEDs). In certain embodiments, the system includes a spectral unit (e.g., an interference filter array, a linear variable filter (LVF), a grating, or a scanning interferometer, e.g., a Fabry-Perot etalon) for dividing a light beam received from the broadband light source (either directly or indirectly, e.g., the light beam entering the spectral unit directly from the source, or after it has passed through the sample) into multiple discrete bands. The system includes a gas flow cell through which the hydrocarbon fluid flows and through which light from the light source (directly or indirectly) and, optionally, from the spectral unit, passes. The system includes an optical detector for receiving the light (directly or indirectly) after transmission through the hydrocarbon fluid flowing through the gas flow cell and for generating a scan signal indicative of spectral information of the detected light over a continuous broadband region (e.g., via a wide-scanning spectrometer, e.g., Fourier transform spectrometer) or over the multiple discrete bands (e.g. obtaining a spectral scan encompassing a near infrared region), where the scan covers a range that is equivalent to, is a subset of, or overlaps, the range from about 800 to about 12 μm.

In certain embodiments, the system includes a processor and a non-transitory computer readable medium storing instructions thereon. The instructions, when executed, cause the processor to identify two or more bands of spectral data from the signal corresponding to the hydrocarbon fluid in the gas flow cell, where the two or more bands are not contiguous (e.g., identify a first band of spectral data from about 1600 nm to about 1900 nm and a second band from about 2200 nm to about 2500 nm). The instructions cause the processor to process each of the two or more non-contiguous bands of spectral data using a first algorithm. The instructions cause the processor to process data from the first algorithm corresponding to each of the two or more non-contiguous bands using a second algorithm (e.g., a chemometric algorithm) to identify and/or quantify the constituents of the hydrocarbon fluid.

In certain embodiments, the first band overlaps at least 100 nm, or at least 150 nm, or at least 200 nm, or at least 250 nm, of the range from 1600 nm to 1900 nm, e.g., without extending beyond the range of 1600 nm-1900 nm by more than 50 nm, more than 100 nm, more than 150 nm, more than 200 nm, or more than 250 nm. In certain embodiments, the second band overlaps at least 100 nm, or at least 150 nm, or at least 200 nm, or at least 250 nm, of the range from 2200 nm to 2500 nm, e.g., without extending beyond the range of 2200 nm-2500 nm by more than 50 nm, more than 100 nm, more than 150 nm, more than 200 nm, or more than 250 nm. The two or more bands may exclude the range 1950 nm to 2150 nm. In certain embodiments, the hydrocarbon fluid is a natural gas, a natural gas liquid, or a biogas.

The two or more non-contiguous bands include at least one near-infrared band (e.g., a band from about 1600 nm to about 1900 nm, and/or a band 2200 nm to about 2500 nm) and a mid-infrared band (e.g., a band that is, or is a subset of, the range from about 3100 nm to about 3600 nm), and the instructions cause the processor to identify a composition-range measurement of at least one component (e.g., from 0.1 to 100 wt. %) and a trace-range measurement of at least another component (e.g., from 0 to 0.1 wt. %). The mid-infrared band overlaps at least 100 nm, or at least 150 nm, or at least 200 nm, or at least 250 nm, or at least 300 nm, or at least 350 nm, or at least 400 nm, or at least 450 nm, of the range from 3100 nm to 3600 nm, e.g., without extending beyond the range of 3100 nm-3600 nm by more than 50 nm, more than 100 nm, more than 200 nm, more than 300 nm, or more than 400 nm.

In certain embodiments, the instructions causes the processor to identify a primary band of spectral data that is equivalent to, is a subset of, or overlaps, the range from about 1600 nm to about 1900 nm and a secondary band that is equivalent to, is a subset of, or overlaps, the range from about 2200 nm to about 2500 nm, where the secondary range is used to identify and/or quantify pentane (e.g., n-pentane) in the hydrocarbon fluid, and where the primary range is used to identify and/or quantify one or more of C1, C2, C3, and C4 in the hydrocarbon fluid. In certain embodiments, the primary band overlaps at least 100 nm, or at least 150 nm, or at least 200 nm, or at least 250 nm, of the range from 1600 nm to 1900 nm, e.g., without extending beyond the range of 1600 nm-1900 nm by more than 50 nm, more than 100 nm, more than 150 nm, more than 200 nm, or more than 250 nm. In certain embodiments, the secondary band overlaps at least 100 nm, or at least 150 nm, or at least 200 nm, or at least 250 nm, of the range from 2200 nm to 2500 nm, e.g., without extending beyond the range of 2200 nm-2500 nm by more than 50 nm, more than 100 nm, more than 150 nm, more than 200 nm, or more than 250 nm.

BRIEF DESCRIPTION OF DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

It is contemplated that methods, systems, and processes described herein encompass variations and adaptations developed using information from the embodiments described herein.

Throughout the description, where systems and compositions are described as having, including, or comprising specific components, or where processes and methods are described as having, including, or comprising specific steps, it is contemplated that, additionally, there are systems and compositions of the present invention that consist essentially of, or consist of, the recited components, and that there are processes and methods of the present invention that consist essentially of, or consist of, the recited processing steps.

The mention herein of any publication, for example, in the Background section, is not an admission that the publication serves as prior art with respect to any of the claims presented herein. The Background section is presented for purposes of clarity and is not meant as a description of prior art with respect to any claim.

Figure 1:
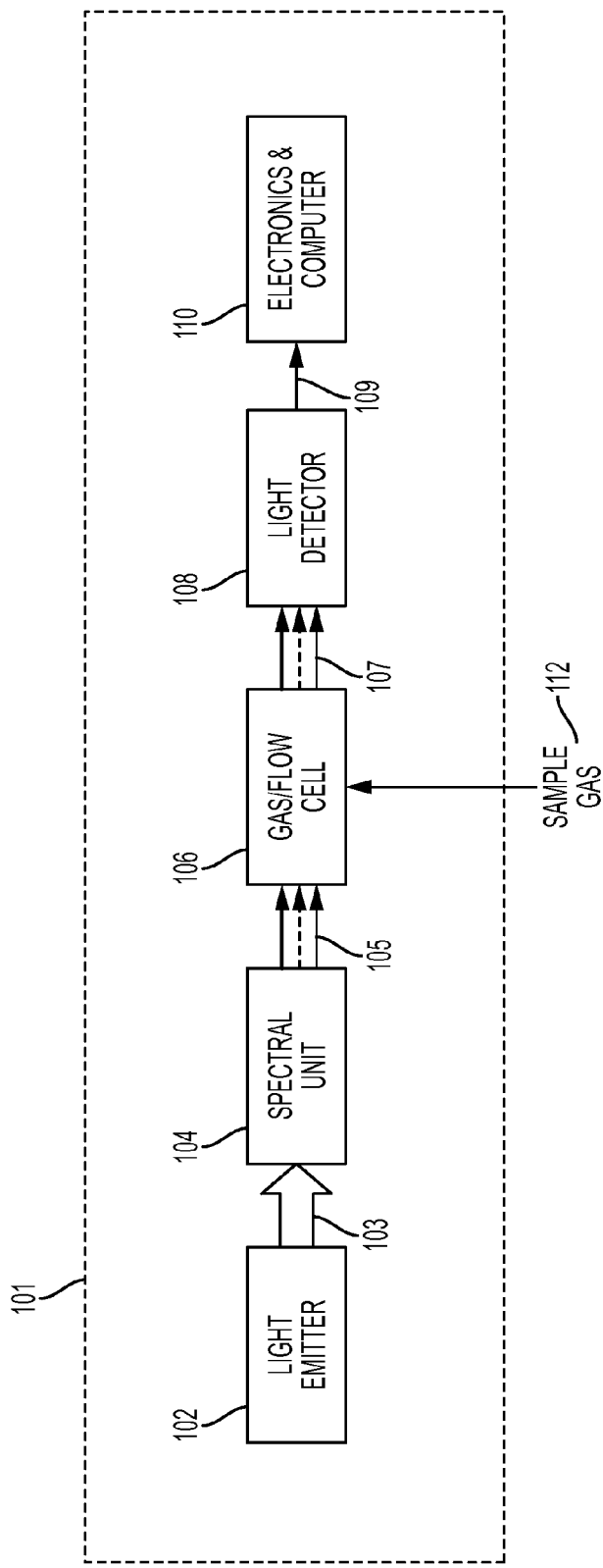
FIG. 1 is a block diagram of the spectroscopic system, according to an illustrative embodiment of the invention.

Referring now to FIG. 1, a diagram of a spectroscopic system 101 for gas analysis is presented. In certain embodiments, the spectroscopic system is a tunable filter spectrometer system, such as described in U.S. Pat. Nos. 8,184,293 and 8,502,981, each entitled, "Methods and Systems for Chemical Composition Measurement and Monitoring Using a Rotating Filter Spectrometer," and U.S. Pat. No. 8,896,839, entitled, "Multiplex Tunable Filter Spectrometer," all of which are incorporated herein by reference in their entireties. For example, the system may be an industrial hydrocarbon composition monitor providing real-time unattended analytics for gas analysis in the natural gas and hydrocarbon processing industries, including, for example, refineries, hydrocarbon processing plants, gas-to-power machines, biogas processes, and fuel gas transportation and monitoring. In certain embodiments, the spectroscopic system includes a Fourier-Transfer Infrared (FTIR) spectrometer, which produces spectra via interferometry. Thus, embodiments include systems for trace/ppm through bulk/% applications, ranging from non-dispersive infrared (NDIR) to laboratory-grade FTIR.

The system 101 of FIG. 1 includes a light emitter 102 for producing a broadband electromagnetic radiation 103. The radiation 103 is in the light domain, such as near infrared (NIR) and mid infrared (MIR). In some implementations, the output radiation of the emitter 102 spans, at least, between 1600 nm and 3600 nm. The light emitter 102 may be made out of a blackbody emitter (such as heated tungsten or Kanthal filament) or light emitting diodes (LED) configured to output the wavelengths of interests.

The spectroscopic system 101 includes a spectral unit 104 to separate the broadband radiation 103 into its wavelength constituents 105. The spectral unit 104 may include an interference filter array, linear variable filter (LVF), a grating, or a scanning interferometer such as that employed in a Fourier transform spectrometer.

In some embodiments, the spectroscopic system includes a gas cell or a flow cell 106 to contain the sample gas 112, sealed with transparent windows, positioned in a direct path of the light beam. The path length of the beam inside the gas cell determines the magnitude of the absorption signal for a given constituent concentration, pressure and temperature. The gas cell is not a necessary part of the spectroscopic system in all embodiments. For example, in certain embodiments, the spectroscopic system 101 is configured as an open path analyzer where the sample gas 112 being analyzed is whatever is present in between the spectral unit 104 and the light detector 108, unconfined by a gas cell. Furthermore, in certain configurations, the gas cell 106 may also be placed in between the light emitter 102 and the spectral unit 104.

In some embodiments, the path length of the gas cell is configured to produce an enhanced or improved signal-to-noise ratio. Furthermore, the gas cell may be equipped with a pressure transducer and/or a temperature transducer to continuously measure pressure and/or temperature of the sample gas in real time. The measured pressure and/or temperature values can be used to correct for the sample pressure and temperature variations. In certain embodiments, systems and/or methods of pressure differential spectroscopy are used for increased accuracy and/or efficiency/speed, for example, the systems and methods described in International Patent Application (PCT) Publication No. WO 2015/054594 entitled, "Systems and Methods for Pressure Differential Molecular Spectroscopy of Compressible Fluids," which is incorporated herein by reference in its entirety.

The optical signal 109 detected by the light detector 108 is then converted to an electrical signal using an amplifier circuit and electronics as part of the electronics and computer 110. The electronics and computer 110 may include an analog-to-digital conversion module to convert the amplified signal a digital signal. The computer 110 includes a memory module that includes instructions for a spectral speciation algorithm, e.g., an algorithm involving multivariate analysis.

The system employs the algorithm to compute the concentration (or other quantification of the amount of) the individual constituents present in the sample gas, such as methane, ethane, propane, etc., which are then reported in a local display unit or communicated to an external monitoring or reporting device through any of various communication devices and protocols such as USB, TCP/IP, Modbus, RS-485, serial communication, wireless, and the like.

In some embodiments, the spectral unit 104 comprises one or more Fabry-Perot etalon or interference filters that transmit(s) a series of narrow band wavelength bands in the wavelength region of interest. Such a component may be constructed from an array of individual filter elements in which each filter transmits a narrow wavelength band.

Figure 2:
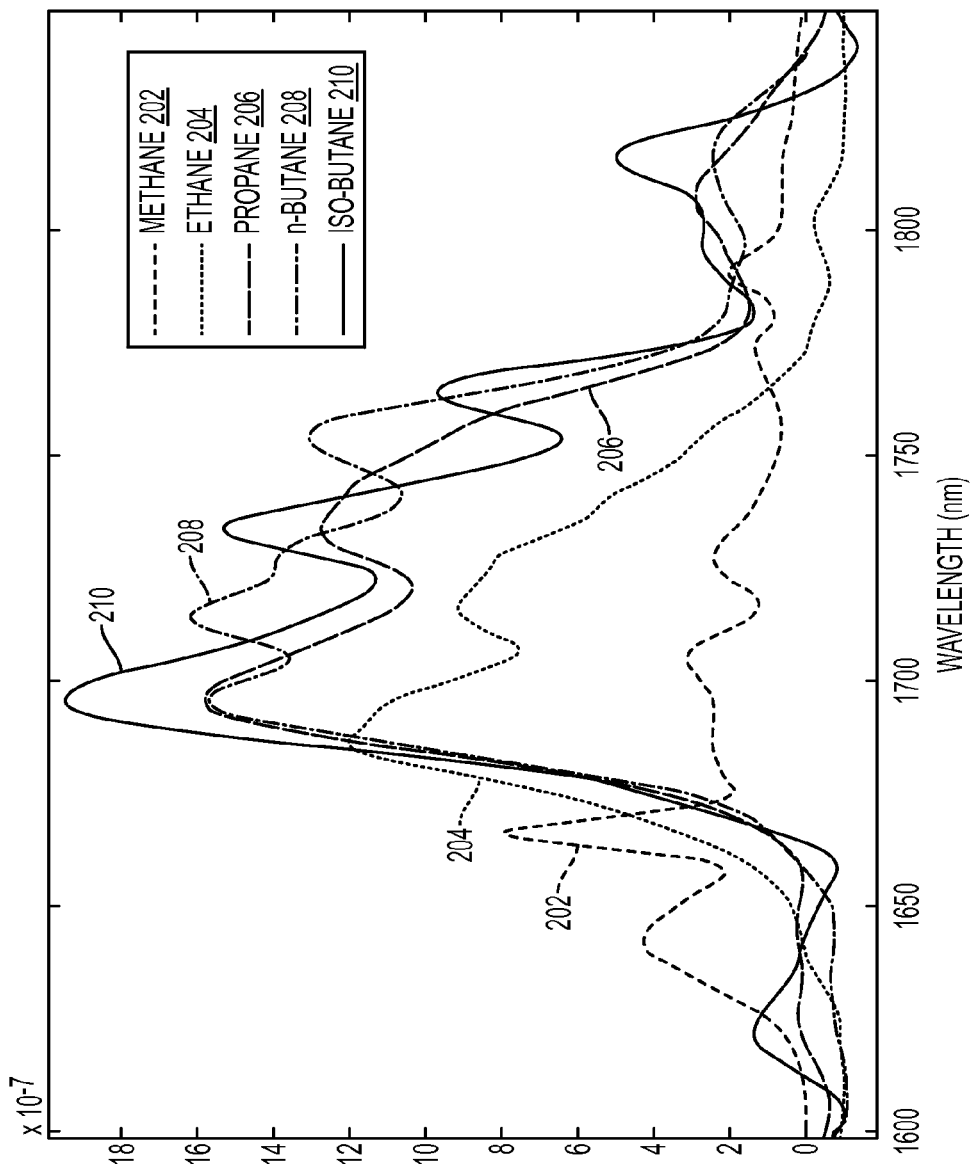
FIG. 2 shows absorption spectra of C1-C4 alkane gases in the near infrared region between 1600 nm and 1900 nm.
Figure 3A:
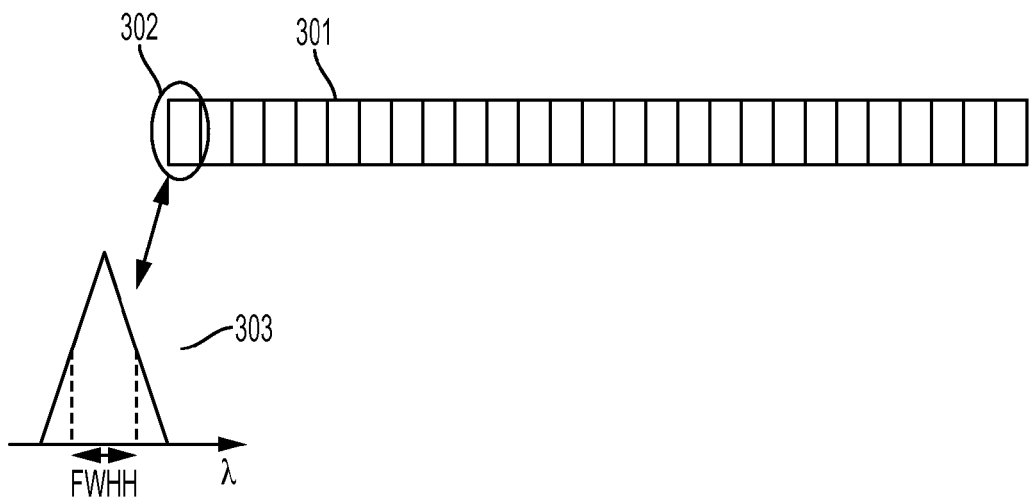
FIG. 3A is a schematic of a spectral unit comprising an interference filter array, according to an illustrative embodiment of the invention.

FIG. 3A is an illustration of a spectral unit comprising an interference filter array 301, according to an illustrative embodiment of the invention. The array 301 includes a number of individual filter elements 302 having bandwidths spanning the operating wavelength range(s) in which each filter 302 transmits only a narrow spectral portion of the light beam. For example, the spectral unit may consist of 60 filter elements, spanning 300 nm between 1600 nm and 1900 nm, in which each filter has a 5-nm bandwidth or resolution. The bandwidth may be defined as full-width-at-half-height (FWHH) of the narrow band transmission spectra (as illustrated in FIG. 2).

The spectral unit 104 is coupled to a light detector 108, which may be configured as a linear type (where the elements are arranged in a one dimensional linear configuration) or a matrix type (where the elements are arranged in a two- or more-dimensional configuration). In such configurations, the spectroscopic system may not employ any moving components.

Alternatively, the filter may be constructed from a bandpass filter element (referred to as a Linear Variable Filter (LVF)) that has been wedged in one direction to cause the transmission wavelength to vary linearly in the direction of the wedge. The spectral unit 104, (configured with the filter array or LVF) is coupled with a light detector 108 that includes a linear photo-detector array. In the case of a LVF, the detector array is a linear type where the elements are arranged in a one-dimensional linear fashion. In the case of a filter array based system, the detector array may be a linear type or a matrix type. A matrix type detector array has elements arranged in a two-dimensional fashion. These configurations allow a spectroscopic system that does not have any moving components.

In certain embodiments using an LVF or a one-dimensional (linear) filter array, a single-element photo-detector is employed. Here, the position of the filter may be varied with respect to the detector is varied to select a particular wavelength band at a given time by moving (e.g., rotating) the filter component.

Figure 3B:
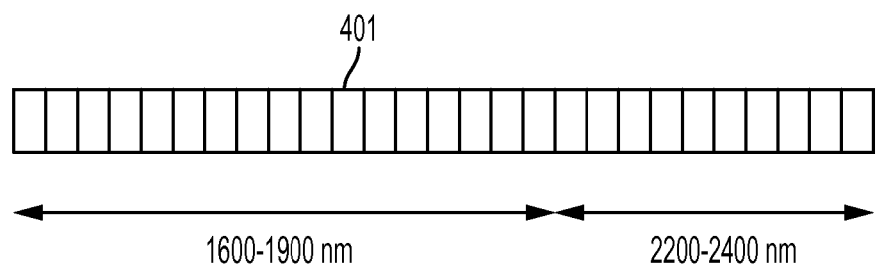
FIG. 3B is a schematic of a filter array comprising multiple non-contiguous spectral regions, according to an illustrative embodiment of the invention.

FIG. 3B is an illustration of a filter array 401 comprising multiple non-contiguous spectral regions (e.g., between 1600-1900 nm and between 2200-2400 nm), according to an illustrative embodiment of the invention.

In certain embodiments, the system utilizes an analysis method based on optical absorption spectroscopy, specifically near infrared (NIR) and/or infrared analysis, targeting electromagnetic absorption due to molecular vibrations.

The method involves first collecting a background/baseline or zero transmission spectrum, which is called the "zero beam." The zero beam may be measured with a gas cell filled with non-infrared-active gas (such as $N_2$, $O_2$, Ar, He) or a gas that has no or negligible absorption in the wavelength region of interest for hydrocarbon analysis (such as air). The gas cell may also be in vacuum for the purpose of measuring the zero beam. In certain embodiments, the zero beam is not independently obtained but rather inferred from a certain sample spectrum, e.g., if the composition of the sample is known or by eliminating portions of the spectral features of the sample in a post-processing stage (such as through polynomial baseline correction). The zero beam is then stored in a storage device in the computer.

During measurement of the sample gas 112, the transmission spectrum of the sample gas 112, called the "sample beam", is then compared with the zero beam. In some embodiments, the sample absorption spectrum is calculated to be: $\log_{10}$(zero beam/sample beam). The sample absorption spectrum is used in the subsequent speciation and quantification algorithm to produce the individual concentration of the sample hydrocarbon gas.

In some embodiments, to obtain a concentration reading of a particular hydrocarbon constituent, the sample absorption spectrum is multiplied with a vector that is orthogonal to the spectra of the other hydrocarbon constituents, called the "component residual spectrum" or CRS. For example, in the case of concentration computation of methane in a C1-C4 alkane matrix, the sample absorption spectrum (which is a 1×n vector, where n is the number of spectral elements) is multiplied with a n×1 CRS vector (obtained, for example, at a precedent "calibration" stage), which is orthogonal to the spectra of ethane, propane, n-butane and iso-butane. In a similar manner, to obtain the ethane concentration of the sample, the sample absorption spectrum is multiplied with an ethane CRS vector (obtained at the calibration stage), which is orthogonal to the CRS spectra (e.g., of methane, propane and butanes). Similar procedures may be employed to compute the concentration of propane, n-butane and iso-butane.

In certain embodiments, gas concentrations are computed by performing least-squares regression of the measured spectrum against the calibration matrices using a classical least squares (CLS) or partial least squares (PLS) approach in which the calibration matrix includes vectors representing basis spectra of the hydrocarbon constituents.

In certain embodiments, the raw sample absorption spectra are treated prior to the speciation and quantification phase of the algorithm in order to remove the baseline noise as well as the high-frequency noise. Spectral baseline noise is usually caused by 'drifts' due to instrument variations such as light source and detector response function variations. Noise may also be caused by light scattering due to the presence of particulates in the sample or by scattering on the optical windows. Spectral baseline noise is generally slow-varying and of low resolution or 'feature-less'. In some implementations, the system employs polynomial fit and correction to remove such spectral noise. In addition, the system may employ digital low-pass filtering in the spectrum pre-treatment stage to remove high-frequency noise (such as that caused by electronics noise).

In certain embodiments, the calibration stage involves collecting the spectra of the individual hydrocarbon constituents. In the above example of the measurement of a C1-C4 alkane matrix, the calibration includes individually collecting the spectra of a calibration gas (e.g., methane, ethane, propane, n-butane and iso-butane). The calibration gas may be a pure mixture or a lower concentration mixture of the gas balanced with a non-absorbing gas (in the wavelength region of interest) such as $N_2$, $H_2$, and/or air. Once obtained, these pure-component spectra are stored and used in the computation of the calibration matrices or the component residual spectrum (CRS).

In certain embodiments, the spectroscopic system operates in the near infrared region between 1600 nm and 1900 nm. This region includes first-overtone vibrations of hydrocarbon molecules, specifically C—H bond vibrations. The spectral features of the light hydrocarbons up to C5 are found to be unique and are employed as "fingerprints" for composition analysis by the speciation algorithm. Furthermore, the absorption spectra are quite linear and additive, even with medium resolution spectroscopic system (1-10 nm resolution), thereby making calibration less cumbersome. Moreover, this wavelength region of analysis may employ light detectors made out of InGaAs (Indium Gallium Arsenide), which is a high-performance detector material that is quite economical, with room-temperature operation.

In certain embodiments, the spectroscopic system 101 operates in the combination band region in the NIR between 2.1 and 2.5 μm. The hydrocarbon spectra in this region provide stronger absorption magnitudes and slightly higher specificity compared to the spectra in the first overtone region. In certain embodiments, the spectroscopic system 101 operates in both the combination band region and the first overtone region to take advantage of the spectral linearity of the first overtone region spectra and the high-specificity of the combination band region spectra.

In certain embodiments, the spectroscopic system 101 operates in the fundamental band region in the mid-IR between 3.1 and 3.6 μm. Since the spectra in this region have orders of magnitude stronger absorption than the NIR spectra, this system may be employed for low-level or trace monitoring applications (such as those requiring ppb, ppm or low-percent, e.g., from 0 to 0.1 wt. % concentration measurement).

In certain embodiments in which the spectroscopic system includes an FTIR spectrometer, the scanned wavelength range provided by the hardware can be very wide, for example, from 1.5 μm to 12 μm. The spectral resolution can be adjustable, thereby providing flexibility for the analysis. The processor can select the multiple spectral bands to include in the speciation and quantification analysis, according to the specific hydrocarbon gas mixture being analyzed.

For example, the multiple spectral bands can be selected to contain spectral signals of all of the hydrocarbon species that need to be measured for a given hydrocarbon gas stream. First, the spectral signals should be at the appropriate magnitudes for the measurement sensitivity and ranges (ppb vs. ppm vs. percent level measurements) for the species in the gas stream to be measured. Second, each of the spectral signals should have one or more unique features to distinguish it from each of the other hydrocarbon species in the stream. One of the bands may be used to meet the first criterion, and another to meet the second criterion. In certain embodiments, a first-pass band selection is made by manually selecting the bands through visual inspection of the features. A fine-tuned set of bands can then be selected through a series of experimentation and regression to produce the most accurate prediction values.

An experiment was performed to demonstrate the improvement in accuracy achieved using two non-contiguous bands for the speciation of n-butane and n-pentane in a hydrocarbon gas mixture, as opposed to a single band. A tunable filter spectrometer with a rotating Fabry-Perot filter was used with a 35-cm gas cell and an extended InGaAs photodetector. A description of illustrative tunable filter spectrometers that can be used with the speciation systems and methods described herein is presented in U.S. Pat. Nos. 8,184,293 and 8,502,981, each entitled, "Methods and Systems for Chemical Composition Measurement and Monitoring Using a Rotating Filter Spectrometer," and U.S. Pat. No. 8,896,839, entitled, "Multiplex Tunable Filter Spectrometer," all of which are incorporated herein by reference in their entireties. In a first configuration, the tunable filter spectrometer was used to scan a single band from 1500 nm to 1780 nm. In a second configuration, the tunable filter spectrometer was used to scan two bands, the first band from 1500 nm to 1780 nm (Band 1) and the second band from 1900 nm to 2200 nm (Band 2).

Figure 4:
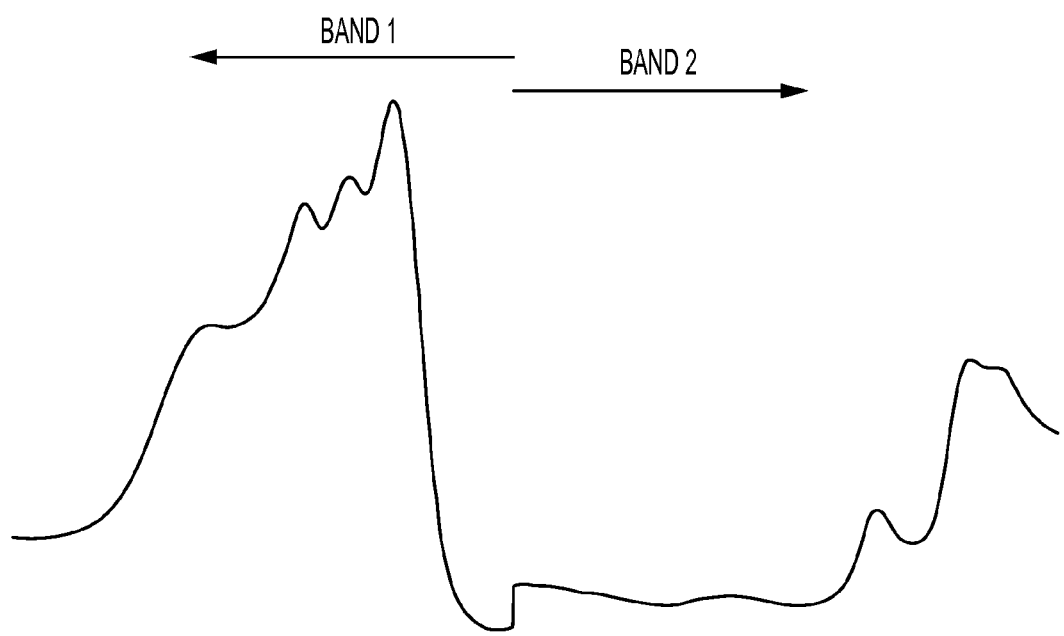
FIG. 4 is a graph depicting a non-contiguous, multi-band spectrum obtained and analyzed according to an illustrative embodiment of the invention.

Accurately speciating and quantifying 0.5% n-pentane in this complex hydrocarbon mixture is especially challenging, particularly considering the presence of n-butane, whose spectrum is very similar to that of n-pentane. The effectiveness of a second band is demonstrated in Tables 1-4 below, and in FIG. 4. FIG. 4 is a graph depicting the non-contiguous, multi-band spectrum obtained from the second configuration (2 bands) for a hydrocarbon gas mixture containing 12% ethane, 10% propane, 10% iso-butane, 10.5% n-butane, 2.5% iso-pentane, and 0.5% n-pentane (Mix 1). The results of the speciation are shown in Table 1. For this experiment, a CLS (classical least squares) calibration algorithm is used with pure-component spectra as the basis spectra. The concentrations predicted using two (non-contiguous) bands results in significantly improved accuracy versus a single band. Similarly, the results for additional mixtures (Mix 2, 3, and 4, in Tables 2, 3, and 4, respectively) show improved accuracy using the multiband approach versus single band.

TABLE 1

| Mix 1 | Actual | 1 band | 2 bands |
| --- | --- | --- | --- |
| Ethane | 12 | 11.55 | 11.83 |
| Propane | 10 | 9.68 | 9.68 |
| iC4 | 10 | 10.33 | 10.33 |
| nC4 | 10.5 | 11.29 | 10.48 |
| iC5 | 2.5 | 2.46 | 2.46 |
| nC5 | 0.5 | −0.87 | 0.51 |

TABLE 2

| Mix 2 | Actual | 1 band | 2 bands |
| --- | --- | --- | --- |
| Ethane | 12 | 11.52 | 11.8 |
| Propane | 10 | 9.68 | 9.68 |
| iC4 | 10 | 10.33 | 10.33 |
| nC4 | 10.5 | 11.19 | 10.41 |
| iC5 | 0.5 | 0.48 | 0.48 |
| nC5 | 2.5 | 1.29 | 2.63 |

TABLE 3

| Mix 3 | Actual | 1 band | 2 bands |
| --- | --- | --- | --- |
| Methane | 5 | 5.36 | 5.18 |
| Ethane | 7 | 6.43 | 6.87 |
| Propane | 5 | 4.79 | 4.79 |
| iC4 | 5 | 5.12 | 5.12 |
| nC4 | 75 | 75.44 | 74.31 |
| nC5 | 0.25 | −1.64 | 0.28 |

TABLE 4

| Mix 4 | Actual | 1 band | 2 bands |
| --- | --- | --- | --- |
| Methane | 5 | 4.97 | 4.93 |
| Ethane | 7 | 7.23 | 7.28 |
| Propane | 5 | 4.83 | 4.83 |
| iC4 | 5 | 5.18 | 5.18 |
| nC4 | 5 | 5.23 | 5.2 |
| nC5 | 4 | 3.31 | 3.8 |

Figure 5:
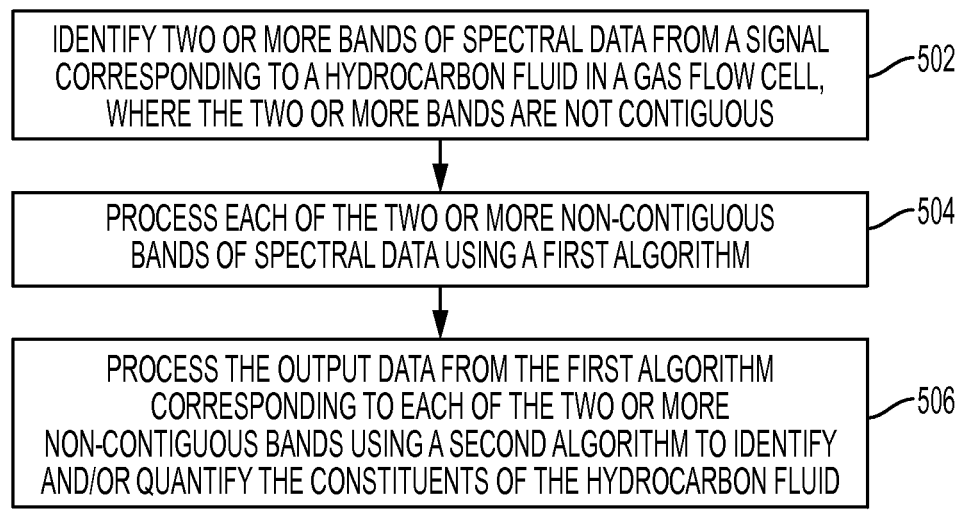
FIG. 5 is a flowchart of a method for speciation and/or quantitative determination of constituents of a hydrocarbon fluid, according to an illustrative embodiment of the invention.

FIG. 5 is a flowchart of a method for speciation and/or quantitative determination of constituents of a hydrocarbon fluid, according to an illustrative embodiment. At step 502, two or more bands of spectral data are identified from a signal corresponding to a hydrocarbon fluid in a gas flow cell, where the two or more bands are non-contiguous. At step 504, each of the two or more non-contiguous bands of spectral data is processed using a first algorithm, e.g., to form a combined spectrum from the two or more non-contiguous bands of spectral data by stitching together the two or more bands. At step 506, the output data from the first algorithm, e.g., the combined spectrum, is processed using a second algorithm (e.g., a chemometric algorithm such as partial least-squares, classical least-square, and/or principal component regression analysis) to identify and/or quantify the constituents of the hydrocarbon fluid.

Figure 6:
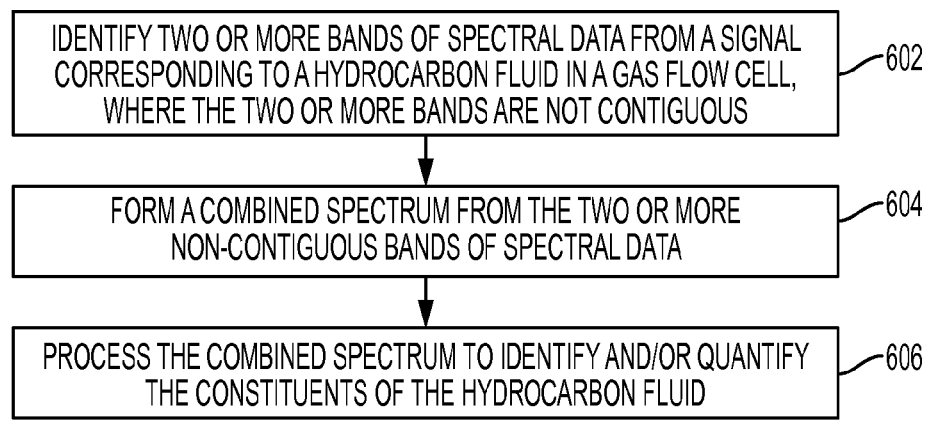
FIG. 6 is a flowchart of a method for speciation and/or quantitative determination of constituents of a hydrocarbon fluid, according to an illustrative embodiment of the invention.

FIG. 6 is a flowchart of a method for speciation and/or quantitative determination of constituents of a hydrocarbon fluid, according to an illustrative embodiment. At step 602, two or more bands of spectral data are identified from a signal corresponding to a hydrocarbon fluid in a gas flow cell, where the two or more bands are non-contiguous. At step 604, each of the two or more non-contiguous bands of spectral data is processed to form a combined spectrum from the two or more non-contiguous bands of spectral data by stitching together the two or more bands. At step 606, the output data from the first algorithm, e.g., the combined spectrum, is processed using a second algorithm (e.g., a chemometric algorithm such as partial least-squares, classical least-square, and/or principal component regression analysis) to identify and/or quantify the constituents of the hydrocarbon fluid.

Figure 7:
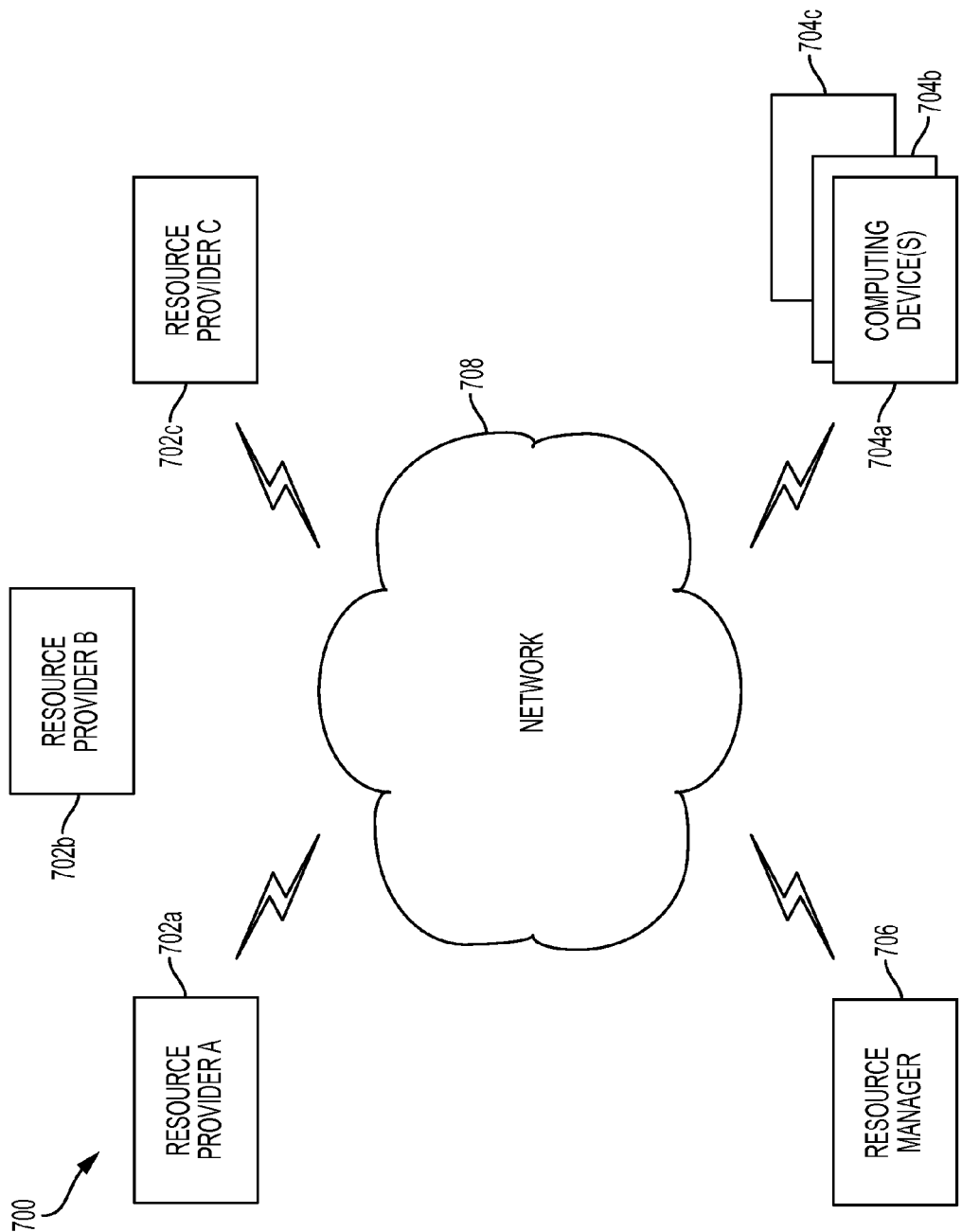
FIG. 7 is a block diagram of an example network environment for use in methods and systems for hydrocarbon gas monitoring, according to an illustrative embodiment of the invention.

As shown in FIG. 7, an implementation of an exemplary cloud computing environment 700 for development of cross-platform software applications is shown and described. The cloud computing environment 700 includes one or more resource providers 702a, 702b, 702c (collectively, 702). Each resource provider 702 includes computing resources. In some implementations, computing resources include any hardware and/or software used to process data. For example, computing resources may include hardware and/or software capable of executing algorithms, computer programs, and/or computer applications. In some implementations, exemplary computing resources include application servers and/or databases with storage and retrieval capabilities. Each resource provider 702 is connected to any other resource provider 702 in the cloud-computing environment 700. In some implementations, the resource providers 702 are connected over a computer network 708. Each resource provider 702 is connected to one or more computing device 704a, 704b, 704c (collectively, 704), over the computer network 708.

The cloud computing environment 700 includes a resource manager 706. The resource manager 706 is connected to the resource providers 702 and the computing devices 704 over the computer network 708. In some implementations, the resource manager 706 facilitates the provisioning of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 establishes a connection between a particular resource provider 702 and a particular computing device 704. In some implementations, the resource manager 706 redirects a particular computing device 704 to a particular resource provider 702 with the requested computing resource.

Figure 8:
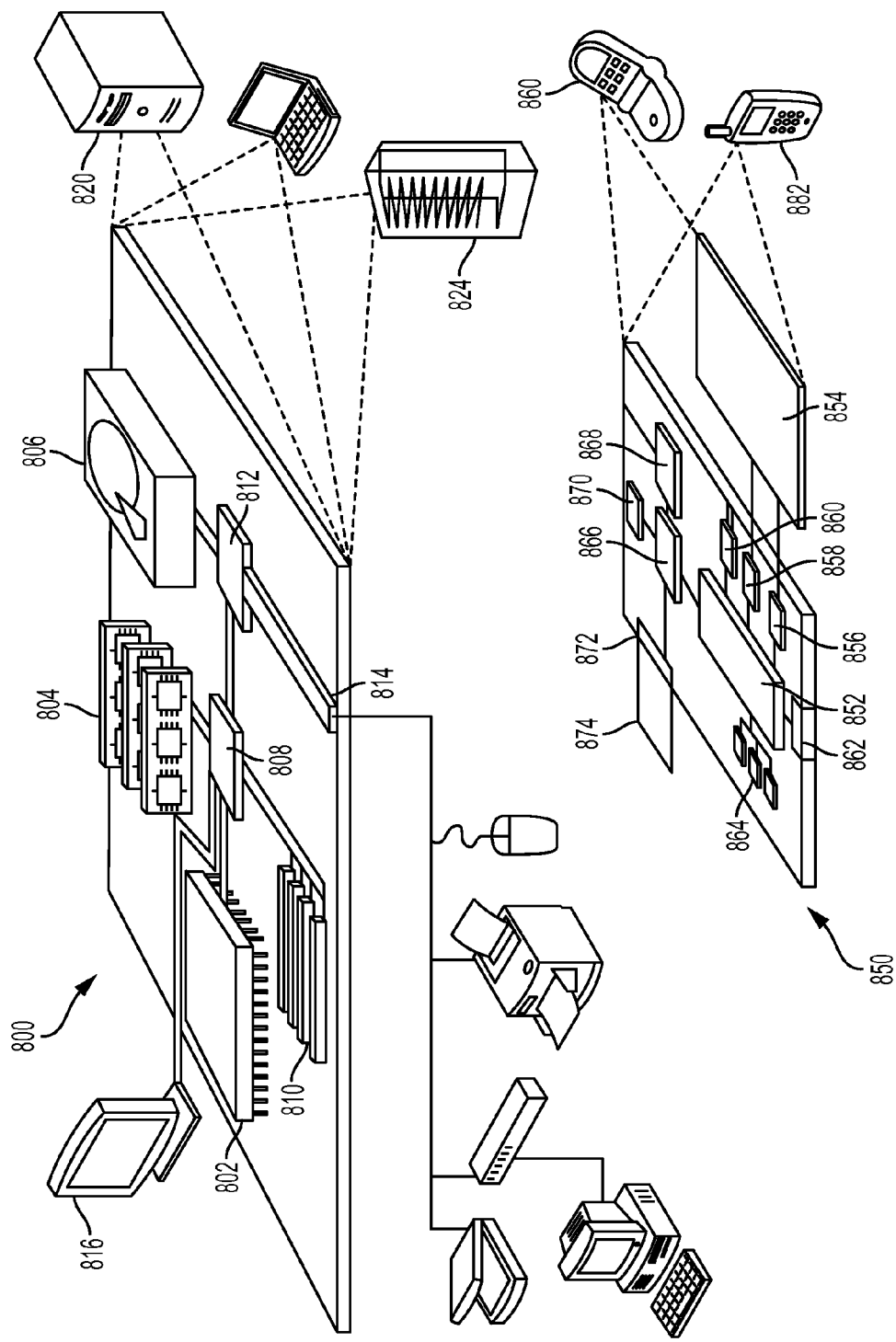
FIG. 8 is a block diagram of an example computing device for hydrocarbon gas monitoring, according to an illustrative embodiment of the invention.

FIG. 8 shows an example of a computing device 800 and a mobile computing device 850 that can be used to implement the techniques described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 814, and a low-speed interface 812 connecting to a low-speed expansion port 814 and the storage device 806. Each of the processor 802, the memory 804, the storage device 806, the high-speed interface 808, the high-speed expansion ports 814, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 814, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 804 may also be provided and connected to the mobile computing device 850 through an expansion interface 812, which may include, for example, a SIMM (Single In Line Memory Module) card interface. The expansion memory 814 may provide extra storage space for the mobile computing device 850, or may also store applications or other information for the mobile computing device 850. Specifically, the expansion memory 814 may include instructions to carry out or supplement the processes described above, and may include secure information also. Thus, for example, the expansion memory 814 may be provide as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. That the instructions, when executed by one or more processing devices (for example, processor 852), perform one or more methods, such as those described above. The instructions can also be stored by one or more storage devices, such as one or more computer- or machine-readable mediums (for example, the memory 864, the expansion memory 814, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 814 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, environments and methods for developing cross-platform software applications are provided. Having described certain implementations of methods and apparatus for supporting the development and testing of software applications for wireless computing devices, it will now become apparent to one of skill in the art that other implementations incorporating the concepts of the disclosure may be used. Therefore, the disclosure should not be limited to certain implementations, but rather should be limited only by the spirit and scope of the following claims.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. The relevant teachings of all the references, patents and patent applications cited herein are incorporated herein by reference in their entirety.

What is claimed is:

1. An industrial hydrocarbon composition monitoring system providing real-time speciation and/or quantitative determination of a plurality of hydrocarbon constituents of a hydrocarbon fluid, the system comprising:
   a broadband light source;
   a gas flow cell through which the hydrocarbon fluid flows and through which or to which light from the light source passes;
   an optical detector for receiving the light after transmission through or reflection from the hydrocarbon fluid flowing through the gas flow cell and for generating a scan signal indicative of spectral information of the detected light over a continuous broadband region or over multiple discrete wavelength bands, where the scan covers a range that is equivalent to, is a subset of, or overlaps, the range from about 800 nm to about 12 µm;
   a processor; and
   a non-transitory computer readable medium storing instructions thereon, wherein the instructions, when executed, cause the processor to:
   identify two or more bands of spectral data from the signal corresponding to the hydrocarbon fluid in the gas flow cell, wherein the two or more bands are non-contiguous;
   combine the two or more non-contiguous bands of spectral data to form a combined spectrum of spectral data; and
   process data from the combined spectrum of spectral data to speciate and/or quantify in real-time two or more hydrocarbon constituents of the hydrocarbon fluid based on the combined spectrum of spectral data.

2. The system of claim 1, wherein the hydrocarbon fluid is a natural gas, a natural gas liquid, or a biogas.

3. The system of claim 1, wherein the hydrocarbon fluid comprises one or more of species C1-C6, in any combination.

4. The system of claim 1, wherein the broadband light source comprises a blackbody source and/or one or more LEDs.

5. The system of claim 1, further comprising a spectral unit for dividing a light beam received from the broadband light source into multiple discrete wavelength bands, wherein the spectral unit and gas flow cell are situated such that the light beam passes from the broadband light source through the spectral unit, then the divided beam passes through the gas flow cell.

6. The system of claim 5, wherein the spectral unit comprises at least one member selected from the group consisting of an interference filter array, a linear variable filter (LVF), a grating, a scanning interferometer, and a Fabry-Perot etalon.

7. The system of claim 1, further comprising a spectral unit for dividing a light beam received from the broadband light source into multiple discrete wavelength bands, wherein the spectral unit and gas flow cell are situated such that light passes from the broadband light source through the gas flow cell, then through the spectral unit.

8. The system of claim 1, wherein the optical detector comprises a member selected from the group consisting of a wide-scanning spectrometer, a Fourier transform infrared (FTIR) spectrometer, and a non-dispersive infrared (NDIR) detector.

9. The system of claim 1, wherein there is at least a 50 nm separation between the nearest ends of two bands of the two or more bands.

10. The system of claim 1, wherein the instructions cause the processor to identify a first band of spectral data that is a subset of 1300 nm to 1800 nm and a second band of spectral data that is a subset of 1850 nm to 2500 nm.

11. The system of claim 10, wherein the instructions cause the processor to identify a first band of spectral data spanning from about 1500 nm to about 1780 nm and a second band of spectral data spanning from about 1900 nm to about 2200.

12. The system of claim 1, wherein the hydrocarbon fluid comprises at least n-pentane and the instructions cause the processor to speciate and quantify at least n-pentane.

13. The system of claim 12, wherein the hydrocarbon fluid comprises at least n-pentane and n-butane, and the instructions cause the processor to speciate and quantify at least n-pentane and n-butane.

14. The system of claim 13, wherein the hydrocarbon fluid contains no greater than 1.0% n-pentane.

15. The system of claim 13, wherein the hydrocarbon fluid contains at least 5% n-butane.

16. The system of claim 1, wherein the instructions cause the processor to identify a first band of spectral data that is a subset of 1600 nm to 1900 nm and a second band of spectral data that is a subset of 2100 nm to 2600 nm.

17. The system of claim 16, wherein the hydrocarbon fluid comprises at least one C6-or-higher species and the instructions cause the processor to speciate and quantify the C6-or-higher species.

18. The system of claim 1, wherein the two or more bands comprise a band from about 3100 nm to about 3600 nm, and the instructions cause the processor to speciate and quantify a component of the hydrocarbon fluid that is present in a concentration no greater than 0.1%.

19. The system of claim 1, wherein the instructions cause the processor to identify a bulk composition-range measurement of at least one component and a trace-range measurement of at least another component,
wherein the bulk composition-range measurement of at least one component is from 0.1 to 100 wt. % and
wherein the trace-range measurement of at least another component is from 0 to 0.1 wt. %.

20. The system of claim 1, wherein the two or more non-contiguous bands comprise at least one near-infrared band and a mid-infrared band, and wherein the instructions cause the processor to identify a bulk composition-range measurement of at least one component and a trace-range measurement of at least another component,
wherein the bulk composition-range measurement of at least one component is from 0.1 to 100 wt. % and
wherein the trace-range measurement of at least another component is from 0 to 0.1 wt. %.

21. The system of claim 1, wherein the instructions cause the processor to identify a primary band of spectral data that is equivalent to, is a subset of, or overlaps, the range from about 1400 nm to about 1900 nm and a secondary band that is equivalent to, is a subset of, or overlaps, the range from about 1900 nm to about 2500 nm, wherein the secondary range is used to identify and/or quantify pentane in the hydrocarbon fluid, and wherein the primary range is used to identify and/or quantify one or more of C1, C2, C3, and C4 in the hydrocarbon fluid.

22. The system of claim 1, wherein the instructions cause the processor to:
form a combined spectrum from the two or more non-contiguous bands of spectral data; and
process the combined spectrum to identify and/or quantify the two or more hydrocarbon constituents of the hydrocarbon fluid.

23. The system of claim 1, wherein the instructions cause the processor to quantify the plurality of hydrocarbon constituents of a hydrocarbon fluid.

24. The system of claim 1, wherein the instructions cause the processor to stitch together the two or more non-contiguous bands to make the combined spectrum of spectral data and to process the combined spectrum using a chemometric algorithm to speciate and/or quantify the constituents of the hydrocarbon fluid in real time.

25. A method for speciation and quantitative determination of a plurality of hydrocarbon constituents of a hydrocarbon fluid, the method comprising:
identifying, by a processor of a computing device, in real time two or more bands of spectral data from a signal corresponding to the hydrocarbon fluid in an industrial process line or pipeline comprising a gas flow cell, wherein the two or more bands are non-contiguous;
combining, by the processor, the two or more bands of spectral data to form a combined spectrum of spectral data; and
speciating and/or quantifying, by the processor, two or more hydrocarbon constituents of the hydrocarbon fluid using data from the combined spectrum of spectral data;
generating light from a light source;
directing light from the light source through or to a gas flow cell;
receiving light at an optical detector after transmission through or reflection from the hydrocarbon fluid flowing through the gas flow cell; and
generating the signal corresponding to the hydrocarbon fluid in the gas flow cell.

26. The method of claim 25, wherein the method comprises determining a bulk composition-range measurement of at least one component and a trace-range measurement of at least another component,
wherein the bulk composition-range measurement of at least one component is from 0.1 to 100 wt. %, and
wherein the trace-range measurement of at least another component is from 0 to 0.1 wt. %.

27. The method of claim 25, wherein the speciating and quantifying step comprises:
forming, by the processor a combined spectrum from the two or more non-contiguous bands of spectral data; and
processing, by the processor, the combined spectrum to identify and/or quantify the two or more hydrocarbon constituents of the hydrocarbon fluid.

28. The method of claim 25, comprising:
displaying or causing to be displayed a graphical representation of the two or more hydrocarbon constituents of the hydrocarbon fluid via a graphical user interface of the computing device.

29. The method of claim 25, comprising quantifying, by the processor, the plurality of hydrocarbon constituents of a hydrocarbon fluid.

30. The method of claim 25, comprising stitching together, by the processor, the two or more non-contiguous bands to make the combined spectrum of spectral data and processing, by the processor, the combined spectrum using a chemometric algorithm to speciate and/or quantify the constituents of the hydrocarbon fluid in real time.

* * * * *

UNITED STATES PATENT AND TRADEMARK OFFICE
CERTIFICATE OF CORRECTION

PATENT NO. : 9,958,380 B2  
APPLICATION NO. : 14/753366  
DATED : May 1, 2018  
INVENTOR(S) : Vidi Saptari Page 1 of 1

It is certified that error appears in the above-identified patent and that said Letters Patent is hereby corrected as shown below:

In the Assignees item (73), please delete "CA (US)" and replace with --(CA)-- therefor.

Signed and Sealed this  
Twelfth Day of June, 2018

Andrei Iancu  
*Director of the United States Patent and Trademark Office*